United States Patent [19]

Henson

[11] Patent Number: 5,792,905
[45] Date of Patent: Aug. 11, 1998

[54] INBRED CORN LINE NP 982

[75] Inventor: Allen R. Henson, Dewey, Ill.

[73] Assignee: Novartis Corporation, Summit, N.J.

[21] Appl. No.: 727,876

[22] Filed: Oct. 9, 1996

Related U.S. Application Data

[63] Continuation of Ser. No. 543,240, Oct. 13, 1995, abandoned.

[51] Int. Cl.$^6$ .............................. A01H 5/00; A01H 5/10; A01H 4/00
[52] U.S. Cl. ................. 800/200; 800/250; 800/DIG. 56; 800/205; 800/235; 47/58; 47/DIG. 1; 435/412; 435/424; 435/430; 435/430.1
[58] Field of Search ...................................... 800/200, 205, 800/235, DIG. 56; 435/172.3, 172.1, 424, 430, 412

*Primary Examiner*—Gary Benzion
*Assistant Examiner*—Melissa L. Kimball
*Attorney, Agent, or Firm*—Thomas Hoxie

[57] ABSTRACT

According to the invention there is provided an inbred corn line, designated NP 982. The invention thus relates to the seeds of inbred corn line NP 982, to the plants of inbred corn line NP 982 and to methods for producing a corn plant produced by crossing inbred line NP 982 with itself or with another corn plant. The invention further relates to hybrid corn seeds and plants produced by crossing inbred line NP 982 with another corn line. Particularly the invention provides a novel hybrid corn plant, designated N7590 produced by crossing inbred NP 982 with another Northrup King proprietary inbred corn line.

17 Claims, No Drawings

INBRED CORN LINE NP 982

This is a CONTINUATION of application Ser. No. 08/543,240, filed on Oct. 13, 1995 now abandoned.

BACKGROUND OF THE INVENTION

This invention relates to the field of corn breeding. More specifically the invention is related to a new and distinctive corn inbred line designated NP 982 and to hybrids made by using NP 982 as a parent.

Corn (*Zea mays*) is a valuable and important field crop. Thus, plant breeders are continually developing new and superior corn inbred lines for production of high yielding, agronomicly sound hybrids. The goal of the plant breeder is to combine in a single variety or hybrid an improved combination of desirable traits from the parental germplasm. These traits may include maximized yield, resistance to disease and insects, tolerance to drought, heat and other environmental stresses, and better agronomic quality.

Corn hybrid development requires the development of homozygous inbred lines, the crossing of these lines, and the subsequent evaluation of those crosses. Pedigree, backcross, and recurrent selection breeding methods are used to develop inbred lines from breeding populations. Breeding programs combine the genetic backgrounds from two or more inbred lines or various other genetic sources into breeding pools from which new inbred lines are developed by self pollination and selection of desired phenotypes. The new inbred lines are crossed with other inbred lines, and hybrids from these crosses are evaluated to determine which have commercial potential.

Once the inbred parents that give a superior hybrid are identified, the hybrid seed can be reproduced indefinitely as long as inbred parent homogeneity is maintained. Corn hybrids may be either single cross hybrids, produced when two inbred lines are crossed to produce the $F_1$ progeny; or double cross hybrids, produced from four inbred lines crossed in pairs (A×B and C×D) and then the two $F_1$ hybrids are crossed again (A×B)×(C×D); or three way cross hybrids produced by crossing a single cross (A×B) to a third inbred (C). Numerous references are available on the topic of corn breeding and hybrid seed corn production; those skilled in the art of corn breeding and production are well aware of techniques and methods for the development of inbred corn lines and corn hybrids. Reference is made particularly to Corn and Corn Improvement, Third Edition, eds. G. F. Sprague and J. W. Dudley, American Society of Agronomy Monograph No. 18, particularly chapters 8 and 9 the substantive contents of which is hereby incorporated by reference.

SUMMARY OF THE INVENTION

The invention provides a novel inbred corn line 982, designated NP 982. This invention thus relates to the seeds of inbred corn line NP 982, to the plants of inbred corn line NP 982 and to methods of producing a corn plant produced by the crossing of inbred line NP 982 with itself or another corn line. This invention further relates to hybrid corn seeds and plants produced by crossing the inbred line NP 982 with another corn inbred line, and particularly to the hybrid designated N7590.

DEFINITIONS

In the description and examples that follow a number of terms are used; therefore, to provide a clear and consistent understanding of the specification and claims the following definitions are provided.

RK=Round Kernels: the percentage of kernels that do not pass through a 13/64 slotted screen.

HE=Husk Extension: the length (cm) of the husk past the ear tip at maturity.

LL=Leaf Length: the length of the ear leaf measured in cm.

NN=Node Number: the number of nodes of the entire plant.

PLT HT=Plant Height. The measure of the height of the plant from the ground to the tip of the tassel in cm.

DE=Dropped Ears. The number of ears that have fallen from the plant over all observations.

EAR HT=Ear Height. The measure from the ground to the top developed ear node attachment measured in cm.

PRM=Predicted Relative Maturity. This trait is based on the harvest moisture of the grain. The relative maturity rating is based on a known set of checks and is referred to as the Minnesota Relative Maturity Rating System.

MST=Harvest Moisture. The moisture is the actual percentage moisture of the grain at harvest.

STK (BR)=The percentage of plants broken below the ear at harvest.

YLD=Yield; bushels per acre. The actual yield of the grain at harvest (bu/a) adjusted to 15.5% moisture.

RT=Number of plants lodged (leaning from vertical but not broken).

DETAILED DESCRIPTION OF THE INVENTION

Inbred corn line NP 982 is a yellow dent inbred line with superior characteristics and is best suited as a male in crosses for production of first generation $F_1$ corn hybrids. NP 982 is best adapted to the Central Cornbelt Area of the United States, and can be used to produce hybrids from approximately 112 to 120 days relative maturity based on the Minnesota Relative Maturity Rating System for harvest of grain. The timing between pollen shed and silking is highly synchronous in inbred NP 982. Additionally, NP 982 has demonstrated good specific combining ability with families derived from Iowa Stiff Stalk, for example, B73, B37, B14 and related lines.

Inbred corn line NP 982 was developed from the $F_1$ population (LH123×J8503) by self-pollination and simple pedigreed ear-to-row breeding. Parent LH123 is a well known Holden's Foundation Seed Co. inbred line, and parent J8503 is a Northrup King Co. line derived by selfing within the $F_1$ of Pioneer Brand P3382. Self-pollination and selection were practiced within the above $F_1$ cross for seven generations in the development of NP 982. During the development of the line, crosses of segregating families were made to inbred testers to evaluate combining ability. Inbred line NP 982 can be reproduced by planting seeds of the line, growing the resulting corn plants under self-pollination or sib-pollination conditions with adequate isolation and then harvesting the resulting seed. No variant traits have been observed or are expected in NP 982.

Inbred line NP 982 has been evaluated at numerous research stations across the United States Corn Belt. The line is uniform and stable for all discernible characteristics as described in the following Variety Description, Table 1. The description is based on data collected primarily at Phillips, Nebraska and St. Joseph, Illinois on a maximum of 4 replications and or 10 subsamples. In interpreting the color designation herein, reference is made to the Munsell Glossy Book of Color, a standard color reference.

TABLE 1

VARIETY DESCRIPTION INFORMATION
FOR INBRED LINE NP 982

Type: Dent    Region Best Adapted: Central Corn Belt (US)

A.  Maturity:

Heat Units Silk (HUS): 1516.

$$\text{Heat Units} = \frac{\text{Max Temp} (\leq 86° F.) + \text{Min Temp} (\geq 50° F.)}{2} - 50$$

B.  Plant Characteristics:

Plant height (to tassel tip): 225 cm
Length to top ear internode: 16.4 cm
Ear height (to base of top ear internode): 72.7 cm
Number of tillers: none
Number of ears per stalk: 2.1
Cytoplasm type: normal C.  Leaf:

Color: medium green (Munsell code 5GY4/4)
Angle from stalk (upper half): 19 degrees
Number of leaves (mature plants) above top of the ear: 6
Marginal waves: few
Width (widest point of ear node leaf): 8.3 cm
Sheath Pubescence: few
Longitudinal creases: few
Length (ear node leaf, "LL"): 80.5 cm D.  Tassel:

Number of lateral branches: 3.5
Branch angle from central spike: 30 degrees
Pollen shed: medium
Anther color: green-yellow
Glume color: green-yellow E.  Ear (Husked ear data except where stated otherwise):

Length: 15.6 cm
Weight: 109.7 gm
Midpoint diameter: 37.7 mm
Kernel rows: 14
Silk color: green-yellow
Husk extension: medium
Taper of ear: average
Husk color (fresh): medium green
Husk color (dry): tan
Shank length: 6.7 cm F.  Kernel (Dried):

Size (from ear mid-point):
  Length: 10.2 mm
  Width: 8.3 mm
  Thickness: 4.0 mm
Shape grade (% rounds): 44%
Pericarp color: colorless
Aleurone color: colorless
Endosperm color: yellow
Endosperm type: normal starch
Gm weight/100 seeds (unsized): 24.3

G.  Cob:

Diameter at mid-point: 22 mm
Strength: strong
Color: light red (Munsell Code 5YR5/6)

H.  Disease Resistance and Insect Resistance:

Preliminary data suggest
Northern leaf blight: tolerant
Southern corn leaf blight: tolerant
European corn borer: susceptible
Gray Leaf spot: tolerant TABLE 1-continued

VARIETY DESCRIPTION INFORMATION
FOR INBRED LINE NP 982

Type: Dent    Region Best Adapted: Central Corn Belt (US)

J.  Variety Most Closely Resembling:

| Character | Inbred |
|---|---|
| Maturity | Mo17 |
| Usage | Mo17 |

Inbred Mo17 is a well known and available corn line. Inbred corn line NP 982 may be distinguished from Mo1 7 and other inbred lines by characteristics described in Table 2.

TABLE 2

1994 Variety Comparison Data of
Inbred Line NP 982

| Variety/Line | Silk HU | Pollen HU | Plant Ht. (cm) | Ear Ht. (cm) |
|---|---|---|---|---|
| NP 982 | 1542 | 1508 | 241 | 65 |
| Mo17 | 1582 | 1476 | 220 | 83 |
| NP 8304 | 1572 | 1546 | 228 | 86 |
| B73 | 1513 | 1502 | 235 | 97 |
| B68 | 1628 | 1567 | 227 | 89 |
| # Reps | 10 | 10 | 8 | 8 |
| LSD (0.5) | 43 | 41 | 18 | 12 |
| cv % | 3 | 3 | 7 | 12 |

This invention is also directed to methods for producing a corn plant by crossing a first parent corn plant with a second parent corn plant, wherein the first or second corn plant is a corn plant of the inbred line NP 982. However, both first and second parent corn plant can come from the inbred corn line NP 982. Therefore any methods using NP 982 are part of this invention including self-pollination, backcross-pollination, hybrid breeding and crosses to populations. It may be desirable to use a male-sterile (either cytoplasmic or nuclear) female parent to prevent self-pollination. If the female is not male-sterile, then either physical or chemical steps should be taken to ensure that self-pollination does not occur. Any plants produced using inbred corn line NP 982 as a parent are within the scope of this invention including any plant produced by the use of cells, protoplasts or tissue from NP 982.

An example of a hybrid produced by crossing inbred line NP 982 is hybrid N7590. This hybrid has NP 982 as a male parent and Northrup King inbred line NP 8304 as a female parent. Inbred NP 8304 (also known as W8304) has PVP Certificate No. 8800032 which is hereby incorporated by reference. The techniques used to obtain the corn hybrid seeds and plants are conventional in the seed industry and are well known to those skilled in the art. The two parent lines are planted in pollinating proximity to each other in alternating sets of rows; however, any convenient planting pattern that allows for the free transfer of pollen is acceptable. The plants of both inbred lines are allowed to grow until the time of flowering. At flowering, the tassels are removed from all plants of the female parent. Natural cross-pollination is allowed to occur. Only the ears from the female plants, NP 8304, are harvested to obtain novel $F_1$ hybrid corn seeds N7590 of the present invention. The $F_1$ hybrid corn plants of the invention are obtained by planting the seeds of N7590 at the next proper growing season. The techniques used to obtain the corn hybrid seeds and plants are conventional in the seed industry and are well known to those skilled in the art.

N7590 is a 115 relative maturity (RM) single cross hybrid. N7590 most closely resembles Northrup King Co. hybrid N7992. N7992 is a Northrup King Co. hybrid sold in the Southern Corn Belt and Southeast U.S. N7590 is distinguished from known hybrid N7992 in that N7590 is substantially higher yielding than N7992; N7590 silks about 60 HU sooner than N7992, with comparable plant and lower ear height. N7590 has been compared with various hybrids, and in Table 3 some of these results are indicated.

TABLE 3

Combined Location and Year Performance Data
(1993–1994: Corn Belt Locations Nebraska to Ohio)

| Hybrid | YLD (bu/a) | MST % | STK % | RT % | HUS GDD | PLT HT (cm) | Ear Ht. (cm) | DE # |
|---|---|---|---|---|---|---|---|---|
| P3394 | 159 | 18.9 | 4 | 2 | 1425 | 260 | 117 | 21 |
| N6330 | 151 | 19 | 5 | 1 | 1407 | 253 | 108 | 23 |
| P3245 | 156 | 20.4 | 5 | 1 | 1470 | 269 | 112 | 15 |
| N7448 | 155 | 20.7 | 4 | 2 | 1449 | 274 | 112 | 37 |
| N7590 | 170 | 20.8 | 4 | 1 | 1422 | 275 | 112 | 23 |
| PX9540 | 156 | 21.4 | 5 | 1 | 1440 | 261 | 117 | 28 |
| N7707 | 162 | 22 | 3 | 1 | 1436 | 268 | 104 | 16 |
| N7992 | 163 | 22.6 | 3 | 2 | 1485 | 281 | 129 | 25 |
| N7989 | 146 | 23.1 | 5 | 2 | 1536 | 269 | 123 | 33 |
| LSD | 5 | 0.4 | 1 | 1 | 17 | 5 | 4 | 0 |
| C.V | 10 | 5.3 | | | | | | |
| OBS | 83 | 83 | 65 | 51 | 14 | 30 | 30 | 52 |

N7590 may be further described by characteristics listed in Table 4.

TABLE 4

VARIETY DESCRIPTION INFORMATION FOR HYBRID N7590

Type: Dent         Region Best Adapted: Central Corn Belt
                   (Northrup King Maturity Zone 7)

A. Maturity:

Relative Maturity (RM): 112–116 days
  U.S. Heat Units = 2770
  FAO = 550–600
  Cytoplasm Type; normal B. Preflowering:

Length of first leaf blade: long
  Anthocyanic pigment of seedling: medium
  Juvenile plant:
    color: medium green
    form: planofil
    size: medium C. Flowering Number of leaves: 15
    below ear: 8
    above ear: 7
  Leaf angle from stalk: 30–60 degrees
  Leaf:
    marginal waves: few
    longitudinal creases: none
    color: dark
  Number of tillers: None
  Plant height to tassel tip: 281 cm
  Length of top ear internode: 17 cm
  Second internode:
    width: 24 mm
    length: 9 cm
  Anthocyanic pigment of brace roots: medium
  Shape of tassel: loose
  Number of lateral tassel branches: 6

TABLE 4-continued

VARIETY DESCRIPTION INFORMATION FOR HYBRID N7590

Type: Dent         Region Best Adapted: Central Corn Belt
                   (Northrup King Maturity Zone 7)

Tassel branch angle: 30–45 degrees from vertical
  Length of largest tassel branch: medium
  Anther color: yellow
  Heat units to:
    50% pollen shed: 1424
    50% silk: 1420
  Silk:
    color: green
    length outside of husk: 11 cm
  Fresh husk color: light green
  Ear leaf:
    anthocyanic pigment: medium
    pubescence: medium
    sheath pubescence: light or none
    length: 100 cm
    width: 9.5 cm
  Ear height: 103 cm
  Number of:
    nodes: 12
    anthocyanic nodes: 10
    anthocyanic internodes: 2
    nodes with adventitious roots: 2
  Peduncle length: 14 cm
  Central spike length: medium
  Glume:
    color: green
    band color: green
  Pollen shed: medium
  % of plants with ear wings: 57
  Ear wing length: 11 cm
  Number of ears per stalk: (1.3)

D. Maturity

Husk:
    extension: medium
    at maturity (HE): medium
  Shank:
    length: 6.8 cm
    internode number: 7
  Kernel:
    rows: distinct
    alignment: straight
    row number: 16
  Ear weight: 229 gm
  Kernel:
    100 weight: 28.5 gm
    length: 12.5 mm
    width: 7.5 mm
    thickness: 3.7 mm
    % round kernels (RK): 32.5
  Ear:
    position at maturity: upright
    length: 17.3 cm
    diameter: 46.3 mm
    taper: average
  Cob:
    color: red
    diameter: 28.3 mm
    strength: strong
  Kernel color:
    pericarp: colorless
    aleurone segregation: homozygous
    aleurone: tan
    endosperm: yellow
    kernel crown: light yellow
    kernel body (sides): yellow
  Endosperm type: normal
  % of kernels showing purple plumule tip: none As used herein the term plant includes plant cells, plant protoplasts, plant cell tissue cultures including that from which corn plants fertile or otherwise can be regenerated, plant calli and plant cell clumps, and differentiated forms of plants such as, but not limited to embryos, pollen, stamen, anthers, flowers, kernels, ears, cobs, leaves, stalks, roots, shoots, plantlets, silks and kernels.

Methods of cell and tissue culture and regeneration are well known in the art and described for example in "Plant Tissue Culture Manual: Fundamentals and Application", Ed. K. Lindsey, Kluwer (1991) and in Green and Rhodes, "Plant Regeneration in Tissue Culture of Maize", Maize for Biological Research (Plant Molecular Biology Association, Charlottesville, Va., 1982, pp. 367–372), which are hereby incorporated by reference.

As is well known, corn can be put to a wide variety of uses not only as livestock feed but also for human consumption of corn kernels and as a raw material in industry. Both grain and non-grain portions of the plant are used as a livestock feed for swine, cattle and poultry. In the food industry corn is used in wet and dry milling. In wet milling there is the separation of the germ, hull gluten and starch. Germ is used to produce corn oil and germ cake for feed. Corn starch may be packaged for human consumption or used in food products such as sauces, gravies, puddings, sweeteners, syrups, and baking powder. Other nonedible uses include textiles, paper, adhesives, cosmetics, explosives, corn binders, laundry purposes and agricultural formulations. Dry milling is used to produce breakfast foods, grits, cornmeal and corn flour. Other uses of corn include fuel, in the form of fuel alcohol or ethanol; seed; alcoholic beverages and construction.

DEPOSIT INFORMATION

Deposits of at least 2500 seeds each of inbred NP 982, NP 8304 and hybrid N7590 have been made unrestrictedly available to the public via the American Type Culture Collection (ATCC), Rockville, Md. 20852 USA. The deposit corresponds to ATCC Deposit Nos. 209453, 209540, and 209507, respectively. The seeds deposited with the ATCC are taken from stock maintained by Northrup King since prior to filing this application. This deposit of Inbred Corn Line NP 982, Inbred Corn Line NP 8304 and Hybrid N7590 will be maintained without restriction in the ATCC depository, which is a public depository, for a period of 30 years, or 5 years from the most recent request, or for the enforceable life of the patent, whichever is longer and will be replaced if they become nonviable during that period.

It is claimed:

1. Inbred corn seed designated NP982 having ATCC Accession No. 209453.

2. A corn plant or its plant parts produced by growing the seed of claim 1.

3. Pollen of the plant of claim 2.

4. An inbred corn plant having all the physiological and morphological characteristics of the corn plant of claim 2.

5. A corn plant regenerated from the cells or protoplasts of a culture of corn tissue having a genotype capable of expressing all the physiological and morphological characteristics of the corn plant of claim 2 the seed of which has been deposited and having ATCC Accession No. 209453.

6. A method for producing first generation ($F_1$) hybrid corn seed comprising crossing a first inbred parent corn plant with a second inbred parent corn plant and harvesting the resultant first generation ($F_1$) hybrid corn seed, wherein said first or second parent corn plant is the corn plant of claim 2, the seed of which has been deposited and having ATCC Accession No. 209453.

7. The method of claim 6 wherein said corn plant, the seed of which has been deposited and having ATCC Accession No. 209453, is the male parent.

8. The first generation ($F_1$) hybrid corn plant produced by growing the seed of claim 6.

9. A method for producing hybrid corn seed comprising the steps of a) planting in pollinating proximity seeds of corn inbred line NP982 having ATCC Accession No. 209453 and a second inbred line, not NP982.

10. $F_1$ hybrid corn seed and plants therefrom produced by crossing inbred corn plant NP982 having ATCC Accession No. 209453 with another corn plant that is not NP982.

11. Hybrid seed of claim 10 wherein inbred corn plant designated NP 982 is the male parent.

12. A hybrid corn plant designated N7590 formed by the crossing of inbred corn plants designated NP982 having ATCC Accession No. 209453 and NP8304 having ATCC Accession No. 209540.

13. Seed of the corn plant of claim 12.

14. Hybrid corn seed designated N7590 having ATCC Accession no. 209507.

15. A hybrid corn plant or its parts produced by the seed of claim 14.

16. A hybrid corn plant having all the physiological and morphological characteristics of the corn plant of claim 15.

17. A tissue culture of regenerable cells from the plant of claim 15.

* * * * *